United States Patent [19]

Bird

[11] 4,121,579
[45] Oct. 24, 1978

[54] VENTILATOR AND METHOD
[75] Inventor: Forrest M. Bird, Palm Springs, Calif.
[73] Assignee: Minnesota Mining and Manufacturing Company, St. Paul, Minn.
[21] Appl. No.: 712,677
[22] Filed: Aug. 9, 1976

Related U.S. Application Data

[62] Division of Ser. No. 544,505, Jan. 27, 1975, Pat. No. 3,974,828.

[51] Int. Cl.² ............................................. A61M 16/00
[52] U.S. Cl. .................................................... 128/145.8
[58] Field of Search .......................... 128/145.5–145.8, 128/142.2, 142.3, 188, 203

[56] References Cited

U.S. PATENT DOCUMENTS

| | | | |
|---|---|---|---|
| 2,830,580 | 4/1958 | Saklad et al. | 128/145.8 |
| 3,234,932 | 2/1966 | Bird et al. | 128/145.6 |
| 3,972,327 | 8/1976 | Ernst et al. | 128/145.8 |

Primary Examiner—Henry J. Recla

[57] ABSTRACT

A ventilator with an inhalation phase and an exhalation phase in its operative cycle having an inlet adapted to be connected to a supply of gas under pressure and first, second and third outlets. A servo controller is provided having an inlet and an outlet with control valve means movable between open and closed positions to control the flow of gas from the inlet to the outlet. Means is provided for supplying gas from the first outlet to the patient adapter. An exhalation valve assembly is coupled to the patient adapter and is movable between open and closed positions. Means is provided for supplying gas from the second outlet to the exhalation valve assembly to maintain the exhalation valve assembly in a closed position during the time the gas is being supplied from the outlet of the servo controller. Means is provided for sensing the pressure of the gas in the means for supplying gas from the outlet of the servo controller to the patient adapter and for switching the servo controller from an open position to a closed position when a predetermined pressure is reached. Flow acceleration means is provided for augmenting the flow of gases through the first outlet when the pressure in the first outlet is of a certain predetermined pressure. Fail-safe apneustic plateau means is provided. In addition, expiratory termination circuit means is provided for commencing the inspiratory phase with high constant positive pressures existing in the inspiratory breathing circle.

1 Claim, 11 Drawing Figures

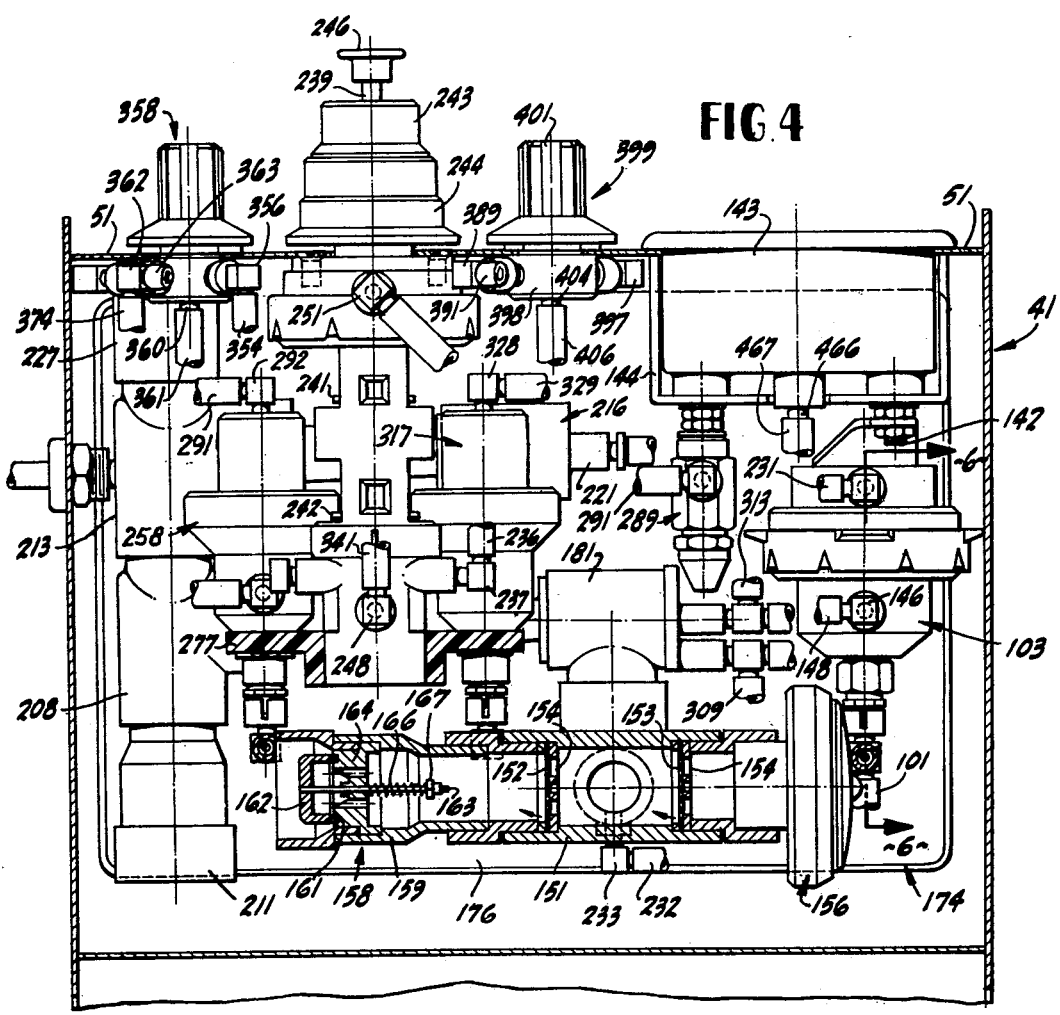
FIG.4
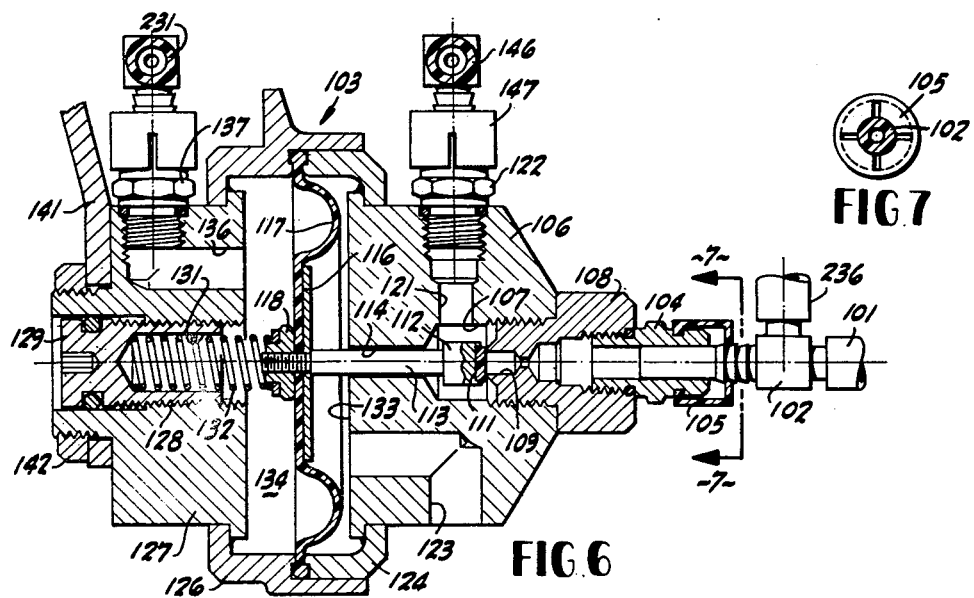
FIG.6
FIG.7

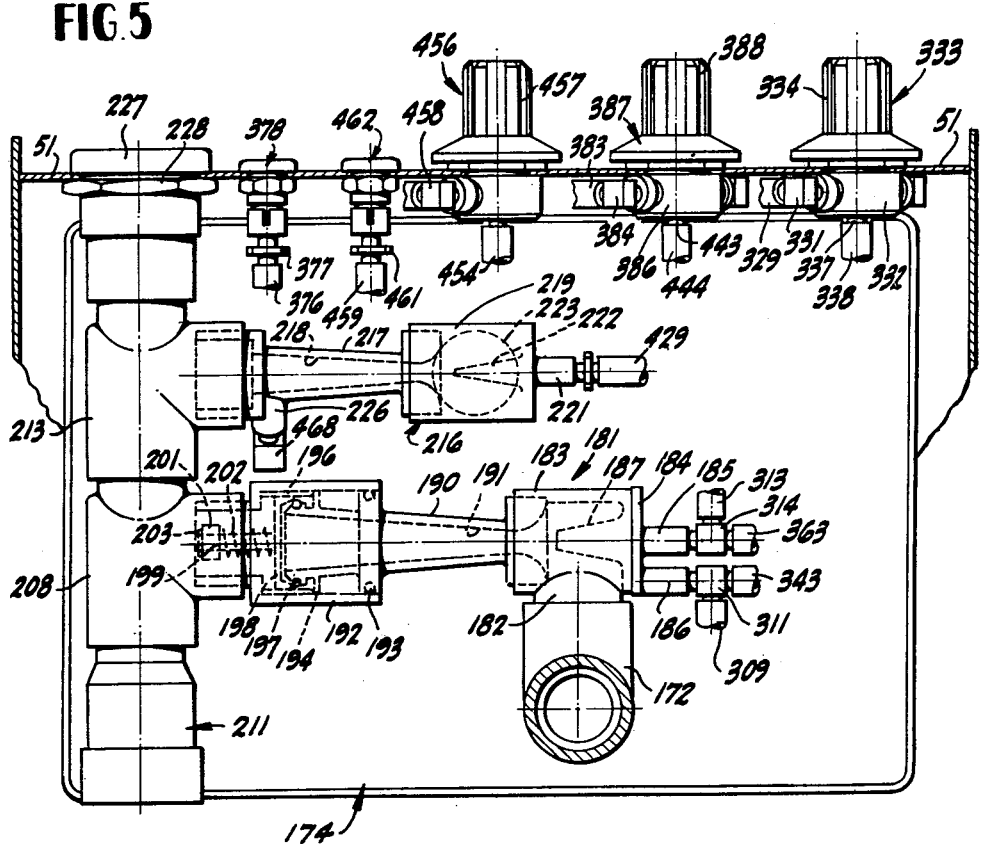
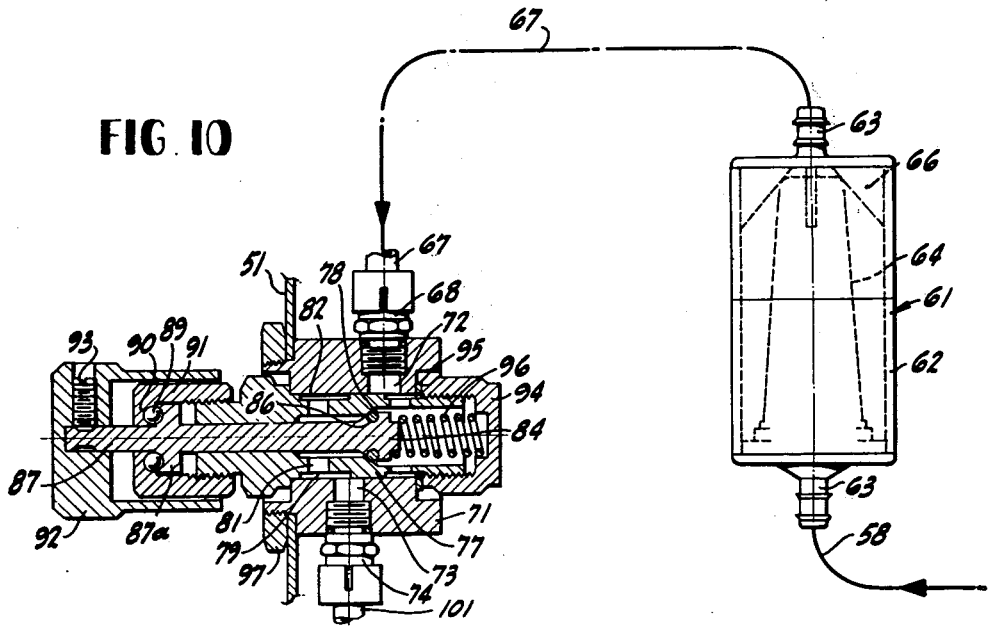

VENTILATOR AND METHOD

This is a division of application Ser. No. 544,505 filed Jan. 27, 1975, now U.S. Pat. No. 3,974,828.

BACKGROUND OF THE INVENTION

Various types of ventilators have heretofore been provided. Many such ventilators have been unduly complicated and expensive. In addition, they have not included certain desirable features such as flow acceleration above predetermined pressures, fail-safe means and the like. There is, therefore, a need for a new and improved ventilator and method which overcomes the above named disadvantages.

SUMMARY OF THE INVENTION AND OBJECTS

The ventilator has an inhalation phase and an exhalation phase in its operative cycle and consists of an inlet adapted to be connected to a supply of gas under pressure and first, second and third outlets. A servo controller is provided which has an inlet and an outlet and control valve means disposed therein movable between open and closed positions to control the flow of gas from the inlet to the outlet of the servo controller. The control valve means is in an open or on position during the inhalation phase of the ventilator and in a closed or off position during the exhalation phase of the ventilator. Means is provided for connecting the inlet of the ventilator to the inlet of the servo controller and for connecting the outlet of the servo controller to the first outlet. A patient adapter is provided, and means is also provided for supplying gas from the first outlet to the patient adapter. An exhalation valve assembly is coupled to the patient adapter and is movable between open and closed positions and in the open position permits gases to flow from the patient adapter to the atmosphere and in a closed position prevents the flow of gases from the patient adapter to the atmosphere. Means is provided for supplying gas from the inlet of the ventilator to the second outlet and means is provided for connecting the second outlet to the exhalation valve assembly to maintain the exhalation valve assembly in a closed position during the time the gas is being supplied from the outlet of the servo controller. Means is provided for sensing the pressure of the gas in the first outlet and for sequencing the servo controller from an open position to a closed position when a predetermined pressure is reached in the first outlet. Flow augmentation means is provided which is connected to the source of gas and for supplying additional gases to the first outlet and includes means for preventing the flow of augmenting gases unless a predetermined pressure is exceeded in the first outlet. Fail-safe apneustic plateau means is provided for controlling the supply of gases to the second outlet from the source to maintain the exhalation valve assembly in a closed position for a period of time beyond the termination of the inspiratory phase. Means is provided for supplying gas under pressure from the source to the third socket for a period of time after commencement of the expiratory phase.

In general, it is an object of the present invention to provide a ventilator and method which is of modular type and which has incorporated therein additional features.

Another object of the invention is to provide a ventilator and method of the above character which can be readily and relatively inexpensively implemented.

Another object of the invention is to provide a ventilator and method of the above character in which flow augmentation is utilized above a predetermined jet pressure in the master venturi delivering gas into the patient breathing circle and in which flow augmentation does not occur at pressures below the predetermined pressure.

Another object of the invention is to provide a ventilator and method of the above character which has fail-safe features.

Another object of the invention is to provide a ventilator and method of the above character in which gases are entrained so that a supply of the same will be available during the inspiratory phase.

Another object of the invention is to provide a ventilator and method of the above character in which the gases are entrained under the control of a demand valve assembly.

Another object of the invention is to provide a ventilator and method of the above character which can be sequenced into an inspiratory phase in the face of relatively high positive pressures in the expiratory breathing circle.

Another object of the invention is to provide a ventilator and method of the above character in which an additional positive pressure flow is provided during the expiratory flow to perform various functions.

Additional objects and features of the invention will appear from the following description in which the preferred embodiments are set forth in detail in conjunction with the accompanying drawing.

BRIEF DESCRIPTION OF THE DRAWINGS

FIG. 4 is a cross-sectional view taken along the line 4—4 of FIG. 1.

FIG. 5 is a cross-sectional view taken along the line 5—5 of FIG. 1.

FIG. 6 is a cross-sectional view taken along the line 6—6 of FIG. 4 showing the demand valve assembly utilized in the ventilator.

FIG. 7 is a cross-sectional view taken along the line 7—7 of FIG. 6.

FIG. 10 is a cross-sectional view taken along the line 10—10 of FIG. 3 showing the master off switch utilized in the ventilator with the associated filter.

DESCRIPTION OF THE PREFERRED EMBODIMENT

Figure 1:
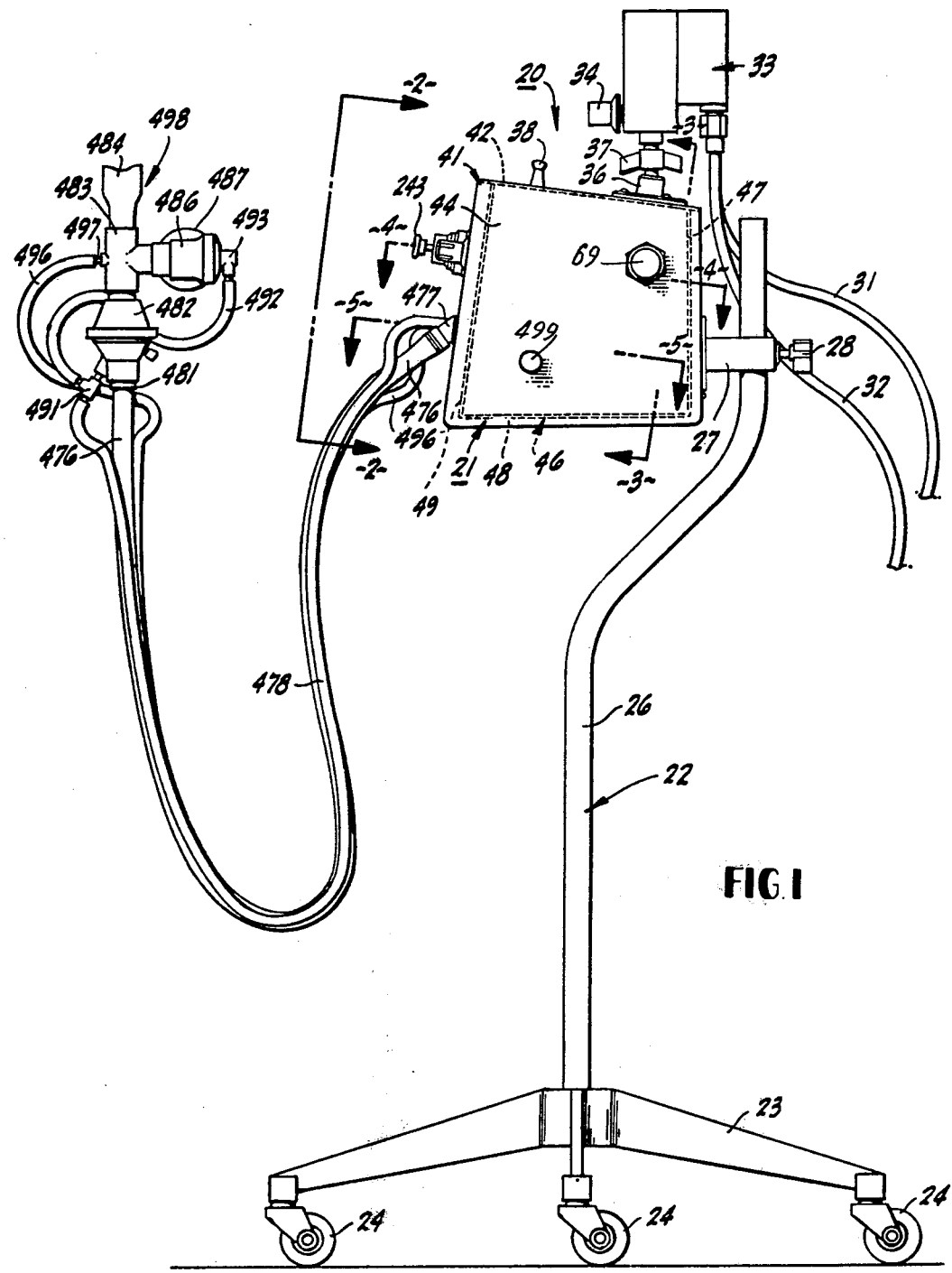
FIG. 1 is a side elevational view of a ventilator incorporating the present invention.
Figure 2:
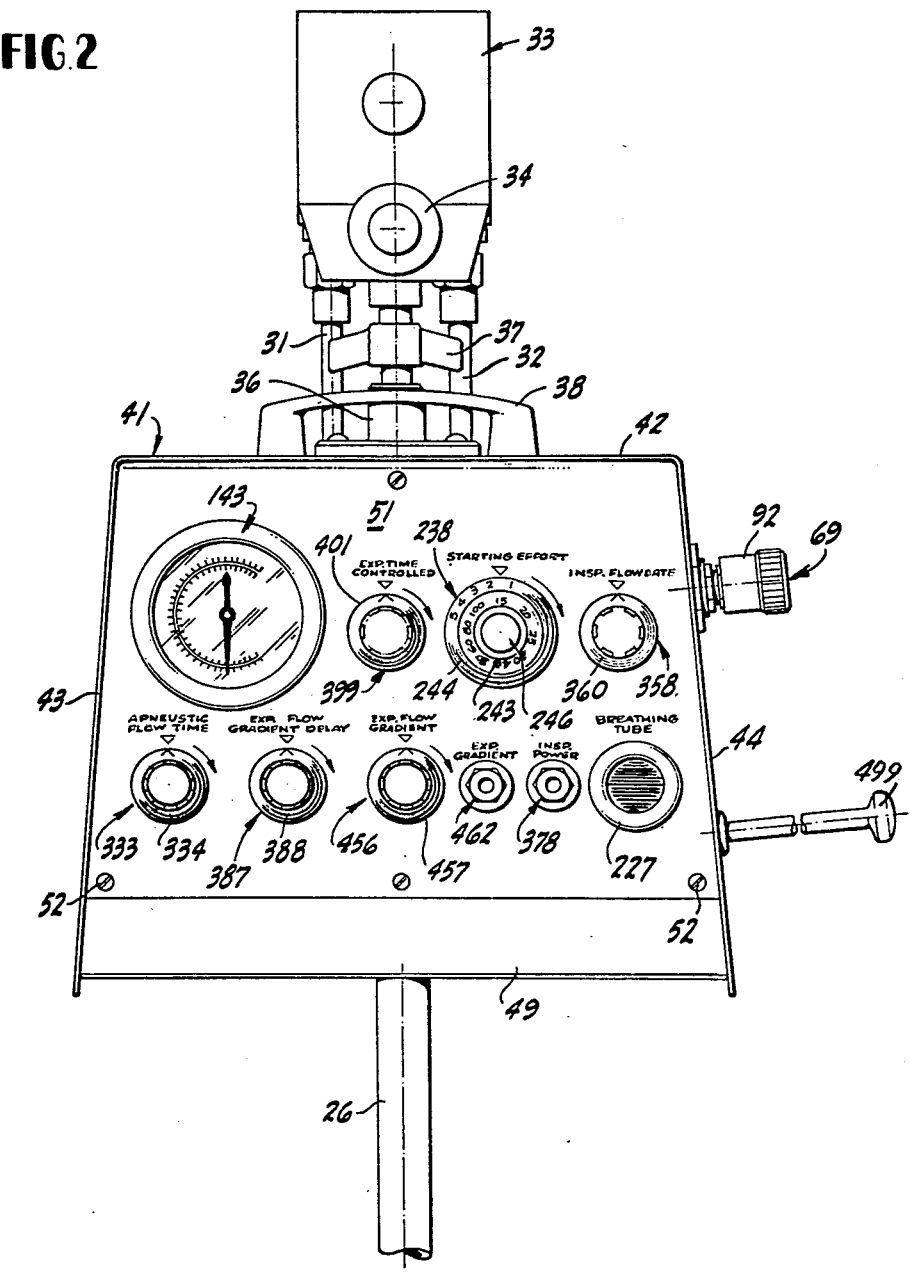
FIG. 2 is a front elevational view looking along the line 2—2 of FIG. 1.

The ventilator 20 incorporating the present invention consists of a cabinet or case 21 which is supported in a suitable manner by stand 22.

The stand 22 is of a conventional type and consists of a four-legged base 23 which is provided with castered wheels 24 mounted on the outer extremities of the four legged base 23. A rigid support rod or post 26 is mounted upon the base 23 and extends upwardly therefrom. The support rod or post 26 is curved as shown so that the cabinet or stand 21 mounted thereon is generally disposed over the center of the base 23. The cabinet or case 21 is provided with a mounting clamp 27 secured to the rear thereof and is adapted to be mounted on the upper extremity of post 26 and is secured thereto by a knob 28.

A suitable source of gas is provided, such as a supply of oxygen under pressure, and a supply of air under pressure. The oxygen and air are supplied through hoses 31 and 32 to an oxygen blender 33 of the type described in U.S. Pat. No. 3,727,627. The blender is provided with a control knob 34 to adjust the percent of oxygen which is supplied to the cabinet. A coupling assembly 36 mounted on the top side of the cabinet is provided with a wing nut 37 which is adapted to be connected to the oxygen blender 33 so that the mixed gas supplied from the blender is supplied to the cabinet or case 21 and utilized therein as hereinafter described. The cabinet or case 21 is provided with a handle 38 on the top side to facilitate handling of the cabinet.

The cabinet or case 21 is formed of sheet metal and consists of a U-shaped member 41 which is provided with a top wall 42 and side walls 43 and 44. The cabinet or case 21 also consists of an L-shaped member 46 which provides a rear wall 47 and a bottom wall 48. It also provides an upwardly extending front wall portion 49. A front panel 51 is mounted within the U-shaped member 41 and is secured to the front wall portion 49 and to the U-shaped member 41 by suitable means such as screws 52.

Oxygen and air supplied through the tubes 31 and 32 from the sources having pressures ranging from approximately 45 to 75 psi and preferably approximately 50 psi. The oxygen and air are blended in a suitable ratio by the oxygen blender 33 which supplies the mixed gas through a nipple 56 carried by the top wall 42. A fitting 57 is removably snapped onto the nipple 56. One end of a tube 58 is connected to the fitting 57 and the other end of the tube 58 is fitted onto one end of a filter 61 (see FIG. 10). The filter 61 is in the form of a hollow cylinder 62 which is closed at both ends and is provided with nipples 63 formed integral therewith. A cup-shaped filter 64, formed of a suitable material such as nylon mesh, has its open end facing one of the nipples 63. The other end of the filter is located upon a plurality of circumferentially spaced radially extending triangular-like supports 66 formed within the cylinder 62. The other nipple 63 on the other end of the cylinder 62 is connected to a tube 67 which is connected to an inlet fitting 68.

A master on and off control switch 69 is mounted in the side wall 44 and consists of a valve body 71 (see FIG. 10) which has an inlet passage 72 and an outlet passage 73 formed therein. The inlet fitting 68 is threaded into the passage or bore 72 whereas the outlet fitting 74 is threaded into the bore or passage 73.

Communication in the body 71 between the bores 72 and 73 is established by a large bore 76, extending axially of the body 71 at right angles to the bores 72 and 73. A valve seat insert 77 is mounted within the bore and is provided with circular valve seat 78. The insert 77 is provided with a bore 79 which establishes communication between the passages 72 and 73 through radially extending passages 81 and annular recesses 82 provided in the insert 77.

Means is provided for interrupting the flow between the passages 72 and 73 and consists of a valve member 84 having an O-ring 86 mounted thereon which is adapted to make sealing engagement with the valve seat 78. The valve member 84 is provided with a valve stem 87 which extends out of the insert 77. The stem 87 has a flange portion 87a formed integral therewith having detents 88 which carry ball bearings 89 that engage detents 90 in a cap 91 threaded onto one end of the insert 77. A knob 92 is mounted on the outer extremity of the stem 87 and is secured thereto by a set screw 93. A cap 94 is threaded on the other end of the insert 77 and engages a seal ring 95 to clamp the insert 77 in the body 71. A spring 96 is seated in the cap and engages one end of the valve member 84. The master control switch 69 is mounted on the front panel 51 and is secured thereto by a nut 97 threaded onto the body 71.

The master control switch 69 is urged towards a closed position by the spring 96. It is moved into an open position against the force of the spring 96 by rotation of the knob 92 to move the flange portion 87a carrying the balls 89 out of the detents 90 to move the valve member 84 to the right as viewed in FIG. 10 to permit communication through the bore 79 and between the passages 72 and 73.

The master switch 89 can be moved to a closed position by rotating the knob 92 in the opposite direction and permitting the balls 89 to drop into the detents 90. This permits the valve member 84 to move to the left as viewed in FIG. 10 to a closed position under the force of the spring 96.

The output fitting 74 is connected to a tube 101, and the tube 101 is connected to a tee-type fitting 102 (see FIG. 6), carried by a demand valve assembly 103. The fitting 102 is mounted in a fitting 104 provided on the demand valve assembly 103 and is retained therein by a cap 105.

The demand valve assembly 103 consists of a body 106 having a bore 107. A fitting 108 is threaded into the bore 107 and has fitting 104 screwed therein. The fitting 108 has a passage 109 extending therethrough which is adapted to be sealed off by a sealing member 111 and carried by the head 112 of a plunger 113 slidably mounted in a bore 114 provided in the body 106. The plunger 113 extends through a circular plate or disc 116 which has bonded thereto the inner portion of a circular diaphragm 117. The diaphragm 117 with the disc 116 is secured to the plunger 113 by a nut 118 threaded on to the plunger 113. The body 106 is provided with a bore 121 which is in communication with the bore 107 and which has a fitting 122 threaded therein. The body 106 is also provided with a passage 123 which is open to the atmosphere and which is in communication with one side of the diaphragm 117 at atmospheric pressure. The outer margin of the diaphragm 117 is clamped between first and second retaining rings 124 and 126 with retaining ring 124 being secured to the body 106 and the retaining ring 126 being secured to a body 127. The body 127 has a centrally disposed threaded bore 128 provided therein which has a fitting 129 threaded into the bore. The fitting 129 is provided with a well 131 which has a spring 132 seated therein. One end of the spring 132 engages the nut 118 to apply a yieldable pressure to one side of the diaphragm 117 and to the plunger 113 to retain the sealing member 111 in engagement with the fitting 108 to interrupt communication between the passage 109 and the passage 121. It can be seen that chambers 133 and 134 are formed on opposite sides of the diaphragm 117. The chamber 133 is in communication with the atmosphere through the passage 123. The chamber 134 is in communication with a passage 136 provided in the body 127. A fitting 137 is threaded into the passage 136. The body 127 is secured to a bracket 141 by nut 142 threaded onto the body 127. The bracket 141 is mounted on threaded studs 142 forming a part of a manometer 143, mounted in the front panel 51 and retained therein by another bracket 144.

The fitting 122 has another fitting 146 mounted therein and is retained therein by a retaining cap 147 identical to cap 105. The fitting 146 is connected to a tube 148 and the tube 148 is connected to fitting 149. The fitting 149 is mounted in a tee 151. One way flapper valves 152 and 153 are mounted in opposite ends of the tee 151. The flapper valves 152 and 153 rest against perforated grids 154 mounted within the tee 151. The flapper valves 152 and 153 are hinged to permit movement toward and away from the grids 154.

An inlet filter 156 is mounted in one leg of the tee 151 opposite the flapper valve 153. An overfill relief valve 158 is mounted in the leg of the tee opposite the flapper valve 152. It includes a generally tubular member 159 which is mounted in the tee 151. The member 159 is provided with an O-ring 161 which forms a valve seat for a valve member 162. The valve member 162 is carried by a valve stem 163 that extends through a perforated plate 164 mounted in the member 159. A spring 166 is mounted on the stem 163 and has one end engaging the plate 164. The other end of the spring 164 is engaged by a nut 167 threaded onto the stem and serves to retain the spring 166 on the stem 163.

The tee 151 is provided with a nozzle 168 which is in communication with the fitting 149 and which is in alignment with the other leg of the tee 151. This other leg of the tee 151 is mounted in a coupling 171. The other end of the coupling 171 is connected to one of the legs of another tee 172. A fitting 173 is mounted in one of the legs of the tee 172. The fitting 173 forms an outlet and inlet for a gas entrainment reservoir 174. As shown, the reservoir 174 is in the form of a flexible plastic bay which has been formed from two sheets 176 of a flexible plastic which have been heat sealed together along their outer margins to provide a gas-tight enclosure. A relatively thin sheet-like mass 177 of a suitable porous plastic foam material is provided within the reservoir 174 and serves to prevent the inner surfaces of the sheets 176 from sticking to each other.

A master venturi assembly 181 is provided which has a fitting 182 that is mounted in one leg of the tee 172. The master venturi assembly 181 includes a cylindrical member 183 which has a cap 184 formed integral therewith on one end thereof. The cap 184 is provided with fittings 185 and 186 which have flow passages and which are in communication with a nozzle 187 formed integral with the cap and centrally disposed within the member 183. The nozzle 187 has a centrally disposed primary passage 188 and secondary passages 189 which are disposed around the central passage 188 (see FIG. 11). The centrally disposed passage 188 is in communication with the fitting 185 whereas the secondary passages 189 are in communication with the fitting 186.

A venturi member 190 is slidably mounted in the other end of the cylindrical member 183 and is provided with a venturi-like passage 191 extending axially thereof. The other end of the venturi member 190 is seated within one end of the gate valve housing 192 and carries an O-ring 193 which establishes a sealing engagement between the housing 192 and the venturi member 190.

The venturi member 190 carries a radially extending flange 194 which engages ribs 196 provided within the interior of the housing 192. Another O-ring 197 is carried by the other extremity of the venturi member 190 and forms a valve seat which is adapted to be engaged by a cup-shaped valve member 198 that is guided by the ribs 196. Means is provided for urging the valve member 198 into engagement with the O-ring 197 to establish a sealing engagement therewith and consists of a valve stem 199 which is slidably mounted within a spider-like structure 201 and the other end engaging the valve member 198. A retaining ring 203 retains the valve stem 199 within the spider-like structure 201. The housing 192 is provided with a fitting 204 which is utilized for purposes hereinafter described.

One end of the gate valve housing 192 is removably mounted in one leg of a tee 208. A gate valve assembly 211 is mounted in another leg of the tee 208 and is identical to the overflow relief valve assembly 158. The gate valve assembly 211 serves as an over pressure governor. It is provided with a valve seat and a valve member, identical to that provided in the overflow relief valve assembly 158.

A tee 213 is mounted in one of the legs of the tee 208. A sensing venturi assembly 216 is mounted in one of the legs of the tee 213. The venturi assembly 216 is provided with a venturi body or member 217 which has a venturi-like passage 218 extending axially of the same and opening into the tee 213. A cylindrical member 219 is mounted on the venturi member 217 and is provided with a fitting 221 which has a passage in communication with a nozzle 222 which is centrally disposed within the cylindrical member 219 and in alignment with venturi-like passage 218. The cylindrical member 219 is provided with a tubular extension 223 which has a fitting 224 mounted therein. The venturi body 217 is provided with a fitting 226 which has a passage therein in communication with the venturi-like passage 218. A breathing tube receptacle 227 is mounted on one of the legs of the tee 213. The breathing receptacle 227 extends through the front panel and is secured thereto by a nut 228 threaded onto the receptacle 227.

A fitting 231 is mounted in the fitting 137 of the demand valve assembly 103. A tube 232 is connected to the fitting 231 and is connected to a fitting 233 which is mounted in the other leg of the tee 151.

Another tube 236 is connected to the fitting 102 on the demand valve assembly 103. The other end of the tube 236 is connected to a fitting 237 mounted in a sequencing servo-cartridge 238. The sequencing servo-cartridge 238 is of the general type described in U.S. Pat. No. 3,753,436 and is of the specific type disclosed in copending application Ser. No. 499,554, filed on Aug. 22, 1974.

Figure 11:
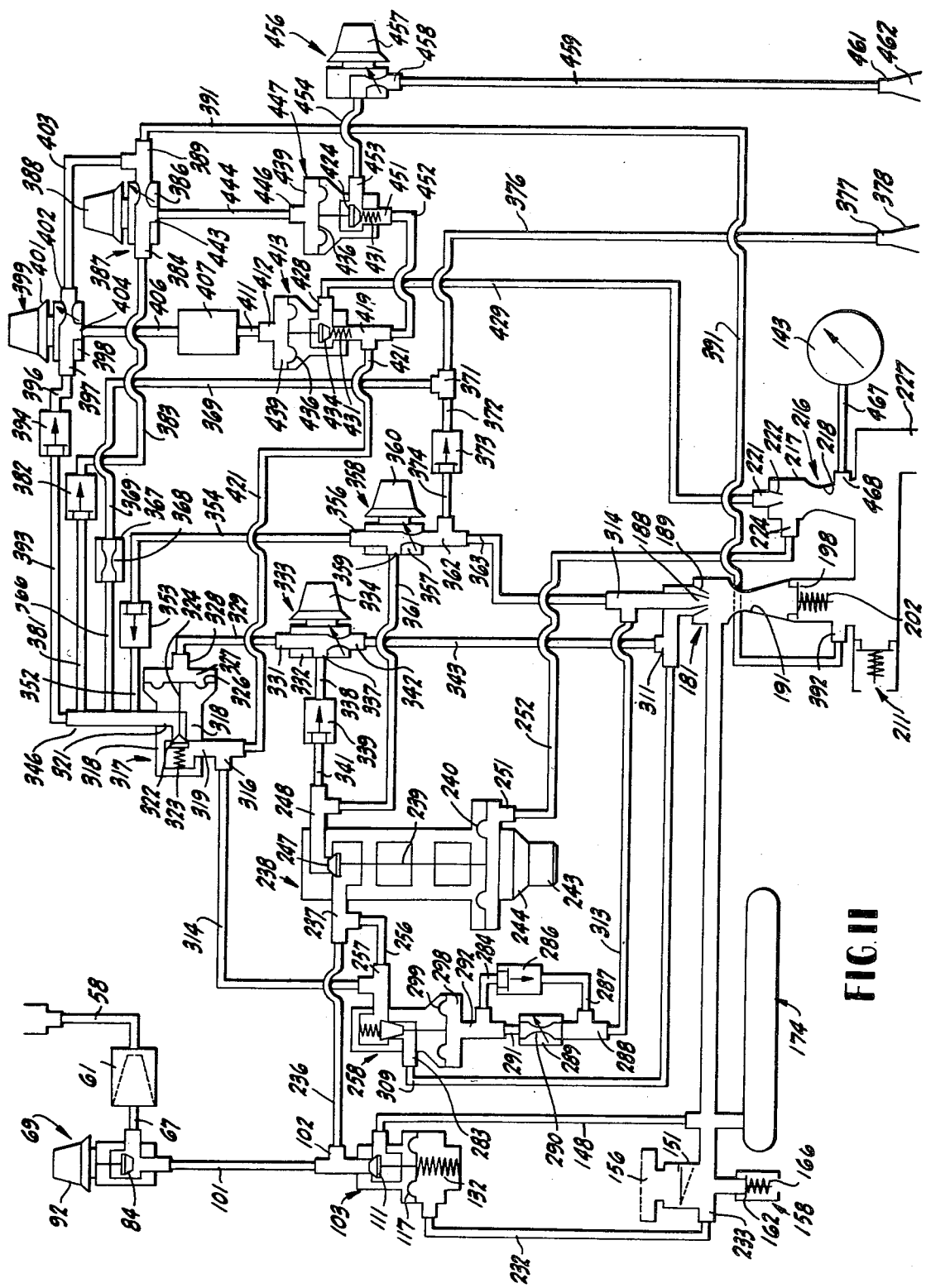
FIG. 11 is a schematic flow diagram of the ventilator.

The master shaft is under the control of a diaphragm 240 (see FIG. 11). It also includes a valve member 247 carried by the master shaft 239 which controls the communication between a fitting 237 and another fitting 248 provided on the sequencing servo cartridge 238. The sequencing servo cartridge 238 is provided with another fitting 251 which is connected to a tube 252. The tube 252 is also connected to a fitting 224 which is mounted in the fitting 223 provided in the venturi assembly 216. The fitting 237 is connected to a tube 256 which is connected to a fitting 257 mounted in a flow accelerator cartridge 258 which is shown in detail in FIG. 8.

Figure 8:
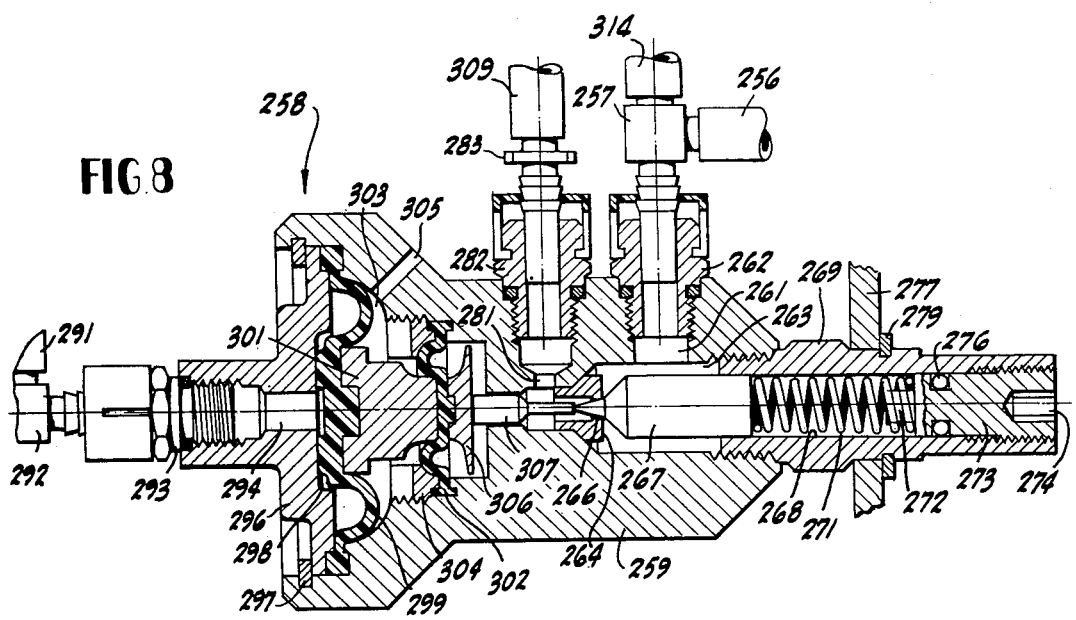
FIG. 8 is a cross-sectional view taken along the line 8—8 of FIG. 3 showing the flow acceleration cartridge utilized in the ventilator.

The flow accelerator cartridge as shown in FIG. 8 consists of a body 259 which is provided with a flow passage 261 into which there is threaded a fitting 262 and in which is mounted the fitting 257. The body 259 is provided with an axially extending bore 263 at one end of which there is mounted a needle valve seat 264. The seat 264 is provided with an orifice 266 which is adapted to be closed by a needle valve 267 moved axially of the bore 263. The needle valve 267 is slidably mounted in a bore 268 provided in a member 269 which is threaded into the bore 263 of the body 259. A spring 271 is seated in the bore 268 and has one end engaging the needle valve 267. The other end of the spring 271 is carried by a boss 272 formed on a screw 273 which is threaded into the bore 268. A tool engaging recess 274 is provided at one end of the screw 273 to permit the screw to be adjusted axially of the bore 268. An O-ring 276 is provided for establishing a seal between the bore 268 and the screw 273.

Figure 3:
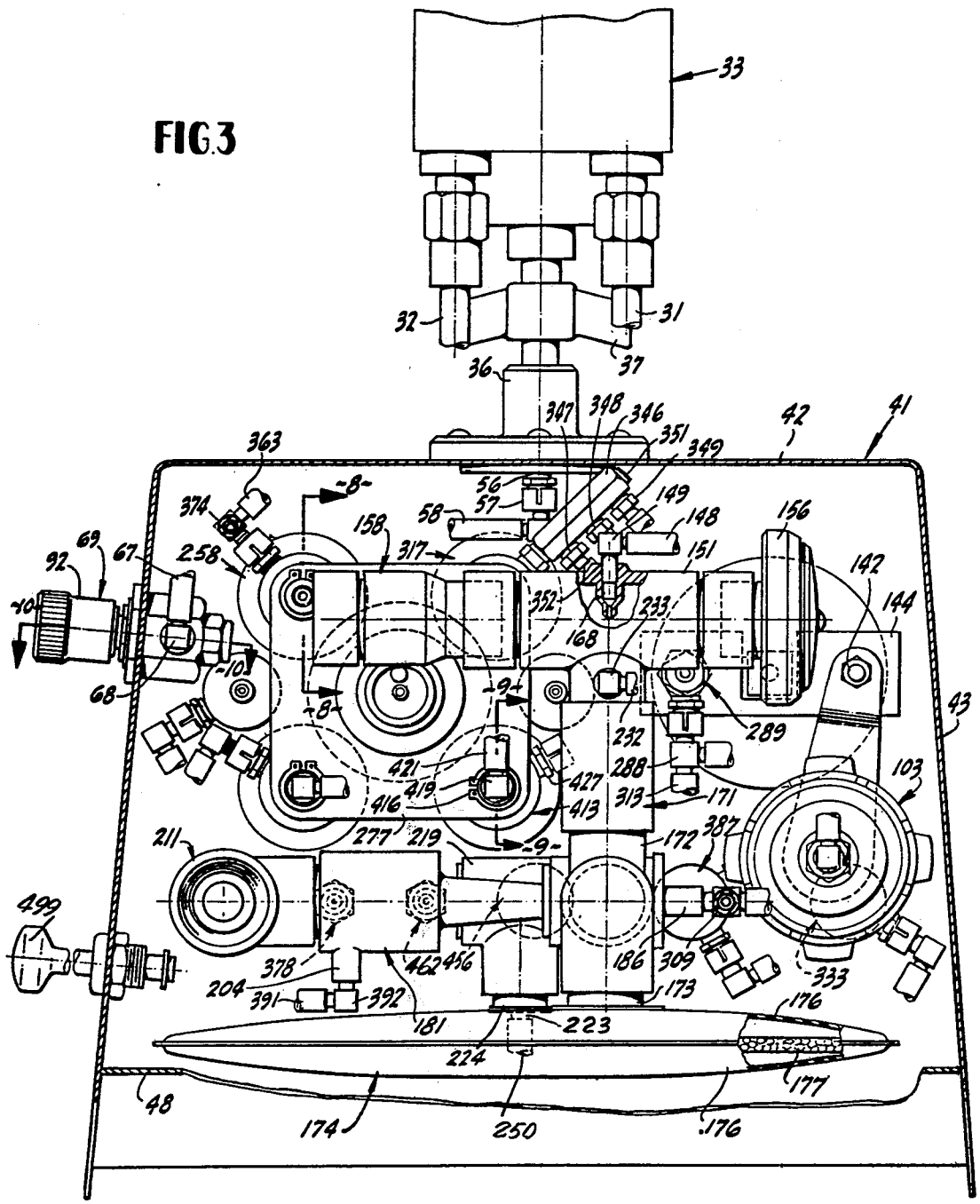
FIG. 3 is a cross-sectional view taken along the line 3—3 of FIG. 1.

Means is provided for securing the flow accelerator cartridge 258 within the cabinet or case 21 and consists of a plate 277 formed of a suitable material such as plastic. The plate 277 is supported by and is mounted with a slip fit on the innermost end of the sequencing servo cartridge 238. The member 269 of the flow accelerator cartridge 258 extends through the upper left hand corner of the plate 277 as viewed from the rear as shown in FIG. 3 and is secured thereto by a lock ring 279.

A bore 281 is provided in the body 259 and is in communication with the bore 263 and extends transversely of the body 259. A fitting 282 is mounted in the bore 281 and another fitting 283 is mounted in the fitting 282. A tube 284 is connected to a one-way check valve 286 and the check valve 286 is connected by a tube 287 to a fitting 288. The fitting 288 is connected to one side of a member 289 carrying an adjustable flow restricting orifice 290. The other side of the member 289 is connected by a tube 291 to a fitting 292. The fitting 292 is also connected to the tube 284. The fitting 292 is mounted in a fitting 293 which is threaded into the bore 294. The bore 294 is provided in a cap 296 which is retained in one end of the body 259 by a retaining ring 297. The bore 294 opens into a chamber 298 provided on one side of a diaphragm 299. The outer margin of the diaphragm 299 is clamped between the cap 296 and the body 259. The diaphragm 299 carries a button 301 which is centrally dispoed thereon. The button 301 engages another diaphragm 302 which is mounted within a chamber 303 provided on the other side of the diaphragm 299 and is retained by a retaining ring 304. The chamber 303 is open to the atmosphere through an orifice 305 provided in the body 259. The diaphragm 302 carries a button 306 which engages an actuator pin 307 that is slidably mounted in the body 259 having its tip adapted to engage the needle valve 267. As hereinafter described, upon the application of pressure to the diaphragm 299 the pin 307 moves the needle valve 267 to the open position against the force of the spring 271.

A tube 309 is connected to the fitting 283 and is also connected to a fitting 311 which is mounted in the fitting 186 carried by the master venturi assembly 181. The fitting 186 is in communication with the secondary jets or passages as hereinbefore described.

A tube 313 is connected to the fitting 288 and is also connected to a tee 314 which is mounted in the fitting 185 provided on the master venturi assembly 181 so that it is in communication with the main passage or primary passage 188 of the master venturi assembly 181. The fitting 257 of the flow accelerator cartridge 258 is connected by a tube 314 to a tee 316 mounted upon an apneustic plateau cartridge 317.

The apneustic plateau cartridge 317 is identical to the cartridge disclosed in the copending application Ser. No. 499,554 filed on Aug. 22, 1974, and as disclosed therein includes a body 318 having flow passages 319 and 321 therein which are in communication with each other through the body. A valve member 322 is provided within the body for interrupting communication between the passages 319 and 321 and is yieldably urged toward a closed psition by a spring 323. Means is provided for moving the valve member 322 to an open position and consists of a valve stem 324 which is moved by a diaphragm 326 provided in the body 318. A chamber 327 is formed in the body on one side of the diaphragm 326 and is in communication with a fitting 328. The fitting 328 is connected by a tube 329 to a fitting 331 mounted in the body 332 of an apneustic flow time control valve assembly 333. This valve assembly 333 is mounted on the front panel 51. The valve assembly 333 is of a conventional type which includes a needle valve (not shown) which can be adjusted by a control knob 334 to control the flow of gas through the body 332. The body 332 is provided with another fitting 337 which is connected by a tube 338 to a one-way check valve 339. The one-way check valve 339 is connected by a tube 341 to a fitting 248 provided on the sequencing servo cartridge 238. The body 332 is also provided with another fitting 342 which is connected by a tube 343 to the fitting 311 of the master venturi assembly 181.

The manifold 346 is mounted upon the body 318 and is in communication with a passage 321 in the body 318. The manifold 346 is provided with four fittings 347, 348, 349 and 351. The fitting 347 is connected by a tube 352 to a one-way check valve 353. The one-way check valve is also connected by a tube 354 to a fitting 356 mounted on the body 357 of an inspiratory flow rate control valve assembly 358 mounted on the front panel 51. The control valve assembly 358 is identical to control valve assembly 333 and is provided with a needle valve (not shown) for controlling the flow of gass therethrough. A fitting 359 is provided on the body 357 and is connected by a tube 361 to the fitting 248 of the sequencing servo cartridge 238. The body 357 is also provided with another fitting 362 which is connected by a tube 363 to the fitting 314 to place them in communication with the principal passage or jet 188 provided in the master venturi assembly 181. The valve assembly 358 is provided with a control knob 360 for adjusting the flow of the gas through the control valve assembly 358.

The fitting 348 provided on the manifold 346 is connected to a tube 366 which is connected to a member 367 having a flow restricting orifice 368 of a fixed size therein. Alternatively, if desired, an adjustable flow control valve (not shown) with a knob for controlling the needle valve can be provided in place of the member 367. The member 367 is connected by a tube 369 to a tee 371. The tee 371 is also connected by a tube 372 to a one-way check valve assembly 373. The one-way check valve assembly 373 is connected to the fitting or tee 362 by a tube 374. The tee 371 is also connected by a tube 376 by a fitting 377 to an inspiratory service socket 378 mounted in the front panel 51.

The fitting 349 on the manifold 346 is connected by a tube 381 to a one-way check valve assembly 382. The one-way check valve assembly is connected by a tube 383 to a fitting 384 which is mounted on a body 386 of an expiratory flow gradient delay control valve assembly 387. The control valve assembly 387 is of the same type as hereinbefore described and includes a needle valve for controlling the flow of gas through the body 386 by adjustment of a control knob 388. A tee 389 is mounted on the body 386 and is connected by a tube 391 to a fitting 392 provided on the master venturi assembly 181.

The fitting 351 of the manifold 346 is connected by a tube 393 to a one-way check valve assembly 394. The one-way check valve assembly 394 is connected by a tube 396 to a fitting 397 provided on the body 398 of an expiratory time control valve assembly 399. As with the previous control valve assemblies it is provided with a control knob 401 for adjusting the rate of flow of gas through the control valve assembly. It is also provided with a fitting 402 which is mounted on the body 398 and is connected by a tube 403 to the tee 389. The body 398 is provided with a fitting 404 which is connected to a tube 406 that is connected to a reservoir 407. The reservoir 407 is connected by a tube 411 to a fitting 412 which is mounted on an expiratory termination cartridge 413.

Figure 9:
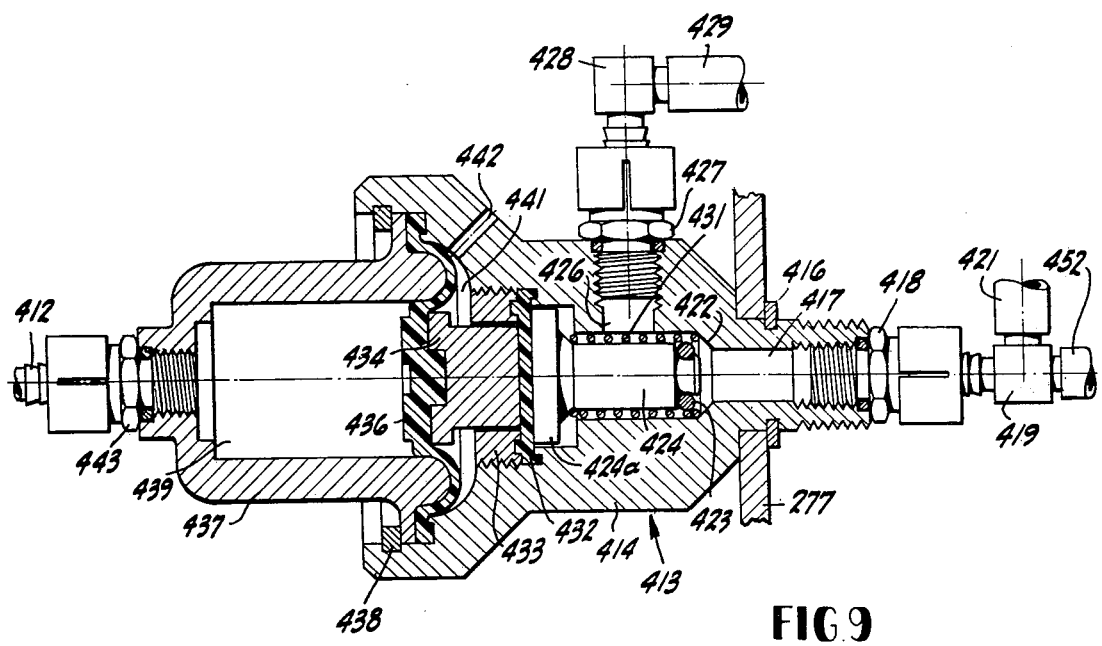
FIG. 9 is a cross-sectional view taken along the line 9—9 of FIG. 3 showing the expiratory termination cartridge utilized in the ventilator.

The expiratory termination cartridge 413 is shown in detail in FIG. 9 and consists of a bell-shaped body 414 which is mounted upon the plate 277 and retained therein by a retaining ring 416. The body 414 is provided with a main flow passage 417 which has a fitting 418 threaded therein. Another fitting 419 is mounted in the fitting 418 and is connected by a tube 421 to the tee 316 of the apneustic plateau cartridge 317. A valve seat 422 is provided in the body 414 and circumscribes the passage 417 and is adapted to be engaged by an O-ring 423 carried by a valve member 424 for interrupting communication between the passage 417 and another passage 426 provided in the body 414 and extending perpendicular to the passage 417. A fitting 427 is mounted in the passage 426. Another fitting 428 is mounted in the fitting 427 and is connected by a tube 429 to the fitting 221 of the servo venturi assembly 216. Suitable means is provided for urging the valve member 424 and the O-ring 423 carried thereby out of engagement with the valve seat and consists of a helical spring 431 mounted on the valve member and having one end engaging the valve seat and having the other end engaging a flanged portion 424a of the valve member 424.

The valve member 424 is engaged by a flexible diaphragm 432 which is retained in the body 414 by a retaining ring 433 threaded into the body. A button 434 is slidably mounted in the retaining ring 433 and is carried by the central portion of a larger diaphragm 436, the outer margin of which is clamped between the body and a cup-shaped cap member 437. The cap member 437 is retained within the body by a retaining ring 438. The cup-shaped cap member 437 provides a relatively large chamber 439 on one side of the diaphragm 436. Another chamber 441 is provided on the other side of the diaphragm 436 and is open to the atmosphere through an orifice 442 provided in the body 414. A fitting 443 is mounted in the cup-shaped member 437 and is in communication with the chamber 437. The fitting 412 previously described is mounted in the fitting 443.

The body 386 of the expiratory flow gradient delay control valve assembly 387 is provided with a fitting 443 which is connected by a tube 444 to a fitting 446 which is mounted on an expiratory flow gradient delay cartridge 447 which has a configuration which is identical to the expiratory termination cartridge 413 and thus will not be described in detail. As can be seen, the fitting 446 is in communication with the chamber 439 on one side of the diaphragm 436. The cartridge assembly 447 is also provided with a fitting 451 which is connected by a tube 452 to the fitting 419 of the cartridge assembly 413. It is also provided with a fitting 453 which is connected by a tube 454 to an expiratory flow gradient valve assembly 456 which is provided with a control knob 457 for controlling the flow of gas therethrough. The control valve assembly 456 is provided with a fitting 458 which is connected by a tube 459 to a fitting 461 that is mounted in an expiratory gradient service socket 462 mounted on the front panel 51.

The manometer 143 is mounted in the front panel 51 as hereinbefore described and has been provided with a fitting 466 which is connected by a tube 467 that is connected to a fitting 468 mounted on the sensing venturi assembly 216.

As shown in FIG. 1, a large breathing tube 476 is removably mounted to the breathing tube receptacle 227. For this purpose, it is provided with an adapter 477 which is mounted on the end of tube 476 and which is fitted into the breathing receptacle 227. A small tube 478 is connected to the inspiratory power socket 378 and is joined with the large tube 476. The other end of the large breathing tube 476 is connected to a fitting 481 that is mounted to a nebulizer 482 of the type described in U.S. Pat. No. 3,172,406. The other end of the nebulizer 482 is connected to one leg of the tee 483. A patient adapter or mouthpiece 484 is mounted in one of the other legs of the tee which is in alignment with the nebulizer 4 An exhaust or exhalation valve assembly 486 is mounted on another leg of the tee 483. A vapor trap assembly 487 is mounted on the exhalation valve assembly 486. The small tube 478 is connected to a tee 491 which is mounted upon the nebulizer 482. Another leg of the tee 491 is connected by a tube 492 to a fitting 493 provided on the exhalation valve assembly 486. Another small tube 496 is connected to the expiratory gradient service socket 462 and also is connected to the large tube 476 so that it bends therewith. The tube 496 is connected to a fitting 497 in a mouthpiece assembly 498 which includes the mouthpiece 484, the exhalation assembly 486 and the nebulizer 482.

Alternatively, if desired, the tube 496 connected to the expiratory gradient service socket may be connected to a pneumatic belt of the type described in U.S. Pat. No. 3,454,000. The belt is fitted snugly around the patient's chest as described in said U.S. Pat. No. 3,454,000. A hanger 499 is slidably mounted in the side wall 44 of the case 21.

Operation of the ventilator may now be briefly described as follows. Let it be assumed that it is desirable to utilize the ventilator for use with a patient. The master on-off switch 69 is turned on by rotation of the knob 92 so that 50 psi source gas under pressure is supplied from the line 58 through the filter 61 through the master on-off valve assembly 69, then through the tube 101. This source gas under pressure is thus supplied to the one side of the demand valve 103. It is also supplied through the tube 236 to the fitting 237 of the sequencing servo cartridge 238, and through the tube 256 to one side of the flow accelerator cartridge 258. In addition, the source gas is supplied through the tube 314 to one side of the apneustic plateau cartridge 317 and also through the tube 421 to one side of the expiratory termination cartridge 413 and one side of the expiratory flow gradient delay cartridge 447 through tube 452.

After the ventilator has been turned on, the patient starts operation of the ventilator by taking a breath which creates a sub-ambient condition in the breathing circuit which includes the mouthpiece 484 and the large breathing tube 476, which sub-ambient condition is supplied through the receptacle 227 to the sensing servo venturi assembly 216. This condition in the sensing venturi assembly 216 is sensed through the tube 252 by the sequencing servo cartridge 238. As described in copending application Ser. No. 499,554, filed Aug. 22, 1974, now U.S. Pat. No. 3,915,164 this causes a sub-ambient condition to be created on one side of the diaphragm 240 of the sequencing servo cartridge 238.

The starting effort for the patient is set by utilizing control dial 244 on the sequencing servo cartridge 238 which carries indicia ranging from 1 to 5. An appropriate setting is 2 which represents a -2cm. of water pressure. The inspiratory positive pressure is set by utilizing the dial or control knob 243 of the same sequencing servo cartridge 238 carrying indicia ranging from 15 to 100 cm. $H_2O$, and can be set within this range. Before starting with the patient, it should be set to 15. The flow rate valve 358 is next adjusted by operating the knob 360 so that the arrow carried thereby is in the 12 o'clock position. The manual control timer knob 243 of the sequencing servo cartridge 238 is pushed in or depressed inwardly and thereafter the oxygen and/or air supplies are turned on to supply oxygen and/or air or a mixture of the same to the ventilator. The manual control timer knob 243 is then pulled out to place the ventilator in the "on" position. At this time there should be a dense flow of aerosol from the nebulizer 482. The manual control timer knob 243 is then pushed in to the ventilator "off" position. For a specific period of time thereafter, between 0.25 to 3 seconds, there should still be a flow of aerosol from the nebulizer 482. This is the apneustic flow time as hereinafter described. The knob 334 is then rotated fully counterclockwise to the minimum (0.25 seconds). The ventilator is then ready for use by the patient.

When a sub-ambient condition is created on one side of the diaphragm of the sequencing servo cartridge 238, the master shaft 239 is moved downwardly as viewed in FIG. 11 to move the valve member 247 out of engagement with its valve seat to permit inspiratory gas under pressure to flow through the sequencing servo cartridge 238 and thence through the fitting 248. Inspiratory gas is supplied through the tube 361 to the inspiratory flow rate control valve assembly 358 through the fitting 362 and then through the tube 363 which is connected to fitting 314 to supply inspiratory gas under pressure through the central passage 188 of the master venturi assembly 181. The jet of gases emanating from the passage 188 will pass down through the venturi passage 191 to cause aspiration of additional gases which will be drawn in from the reservoir 174 and if necessary from the filter 156 and through the large bore tube formed by the tee 151, the coupling 171 and the tee 172. The gases which are supplied through the venturi passage 191 apply a positive pressure to the gate valve member 198 to open the same against the force of the spring 202 to permit the gases to pass through the receptacle 227 and thence through the large tube 476 and then through the nebulizer 482, the tee 483, through the mouthpiece 484 and into the breathing passageways or airways of the patient. At the same time inspiratory gases under pressure are supplied to the inspiratory service socket 378. These gases are supplied from the tee 362 through the tube 374, the one-way valve assembly 373, the tube 372, the tee 371 and thence through the tube 376 to the socket 378. These inspiratory gases are supplied to the small tube through the tee 491, the tube 492 to the exhalation valve assembly 486 to maintain the exhalation valve assembly in a closed position during the inhalation or inspiratory phase of the ventilator.

The gate valve assembly 211 serves as an over-pressure governor and serves to protect the patient from over-pressures as, for example, a pressure above 67 cm. of water to prevent damaging the patient's lungs. The manometer 143 senses the pressure of the gases being supplied to the patient.

Inspiratory gases are also supplied from the fitting 248 through the tube 341, the one-way check valve 339, the tube 338 and then through the apneustic flow time control valve assembly 333 and then through the tube 343 to the fitting 311 and then through the secondary passages 189 of the master venturi assembly 181 to augment the flow of gases through the venturi passage 191 and to the patient following the path hereinbefore described. This inspiratory gas under pressure is also supplied through the tube 329 to one side of the diaphragm 326 of the normally closed apneustic plateau cartridge 317.

At the commencement of the inspiratory phase, the jet of gases supplied through the master venturi assembly 181 causes gases to be drawn in or aspirated from the entrainment reservoir 174 and pushes such gases through the gate valve 198 into the breathing circuit to the patient. By the use of the entrainment reservoir 174, there is an adequate supply of mixed gases which are available for use by the patient during the inspiratory phase and during the period when the source gas is supplied from the source line 58 may be inadequate. In addition, if the patient requires still more gas than that which can be supplied by the entrainment reservoir 174, additional air can be introduced through the filter 156.

As soon as the pressure of the gases in the entrainment reservoir 174 is reduced, this reduced pressure condition is supplied to the demand valve assembly 103 through the tube 232 which causes the diaphragm 117 to be moved against the force of spring 132 to open the valve 111 and to permit source gas to flow from the master on-off control valve assembly 69 through the tube 101, the fitting 102, through the demand valve assembly 103 and through the tube 148 into the entrainment reservoir 174. The demand valve assembly 103 remains open until the entrainment reservoir 174 is filled. Thus, gas will be supplied through the tube 148 during the inspiratory phase and this can continue into the exhalation or expiratory phase at which time gases are not being drawn from the entrainment reservoir 174 by the master venturi assembly 181. As soon as the reservoir is filled, the pressure increases which pressure increase is supplied to the demand valve assembly 103 through the tube 232 to permit the spring 132 to move the valve 111 to the closed position.

It is desirable that the entrainment reservoir 174 be kept as full as possible at all times so that there will be an adequate supply of mixed gases available for the patient. In this way, the proper ratio of mixed gases will be supplied to the patient without the necessity of drawing additional air in through the filter 156.

At the time that inspiratory gases are supplied through the inspiratory flow rate control valve assembly 358 to the main jet or passage 188 of the master venturi assembly, the flow accelerator cartridge 258 is loaded. This is accomplished by inspiratory gases which are supplied from the fitting 314 through the tube 313, the fitting 288, through an adjustable restricted orifice 289 and thence through the fitting 292 to one side of the diaphragm of the flow accelerator cartridge 258.

The needle valve in the adjustable restricted orifice 289 makes it possible to provide an adjustable slope at any pressure gradient across the flow accelerator cartridge. The pressure which must be built up in the chamber 298 to cause the needle valve 267 to move to an open position with respect to the valve seat 264 is determined by the pressure which is applied by the spring 271. This can be adjusted by the screw 273 so that the pressure build-up within the chamber 298 must be a suitable valve as, for example, 18 lbs psi before the valve member 267 will be moved to an open position. Because of the restricted orifice 289, a pressure build-up within the chamber 298 will take a period of time and if the pressure build-up is insufficient to overcome the force of the spring 271, the valve member 267 will remain in a closed position and no additional inspiratory gases will be supplied to the secondary jets 189 to augment the main flow of gases in the patient breathing circuit to the patient adapter 484. Since this is the case, this permits the inspiratory flow rate to be determined exclusively by the inspiratory flow rate control valve assembly 358 at very low rates of flow at pressures below a predetermined pressure as, for example, 18 lbs psi without activating the flow accelerator cartridge 258. Since the average pressure used for intermittent positive pressure breathing type therapy ranges from 12 to 16 lbs psi, this permits approximately 180° rotation of the control knob 360 of the flow rate control valve assembly 358 on the right side of the knob for therapeutic purposes without activating the flow accelerator cartridge. The other 180° of rotation of the knob 360 can be utilized for intensive care applications. For each rate of flow through the control valve assembly 358 which creates pressure of 18 psi or greater, assuming that the spring 271 is adjusted for 18 psi, the rate at which the flow accelerator cartridge 258 opens will be dependent upon the slope established by the adjustable restricted orifice 289 that meters gas into the chamber 298. It can be seen that a slope can be established with each and every pressure drop through the flow accelerator cartridge. This makes possible a rapid build-up of flow acceleration in the breathing circuit but prevents any initial squarewave effect because there is always some retardation in opening of the flow accelerator cartridge 258.

Whenever the inspiratory gas pressure supplied to the chamber 298 in the flow accelerator cartridge 258 exceeds the spring pressure on the diaphragm 299, the valve member 267 is moved to an open position against the force of the spring 271 to permit source gas under pressure which is present in the tube 256 to pass through the flow accelerator cartridge 258 and thence into the tube 309 to the fitting 311 to augment the flow of gases through the secondary passages 189 to thereby increase the flow of inspiratory gases to the patient.

The initial flow of inspiratory gases during the inspiratory phase of the ventilator delivers inspiratory gases into the distal airways or ducts of the patient's lungs. Automatic nebulization occurs during the inspiratory phase because the inspiratory gases must pass through the nebulizer 482. The rate of inspiratory flow determines the volume of inspiratory nebulization. As the flow rate is increased, the pressure behind the primary jet of gases from the nozzle of the master venturi assembly 181 increases causing an increased flow in the breathing circuit.

In the present invention, the inspiratory flow is supplemented or augmented by parallel flows of inspiratory gases, one of which is through the apneustic plateau flow rate control valve assembly 317 and the other of which is through the flow accelerator cartridge 258. The flow through the apneustic plateau flow rate control valve assembly 317, when once it commences as hereinbefore described, continues throughout the inspiratory phase and for a period of time after the end of the inspiratory phase as determined by the setting of the apneustic flow time control valve assembly 333. Thus, there is provided a minimum flow of gases from the nebulizer regardless of the slowing of the inspiratory flow rate near the end of the inspiratory phase. In this manner it is possible to effectively double the volume of particulate delivery from the nebulizer 482 during slow flow techniques.

When a certain pressure is reached in the breathing circuit to the patient during the inspiratory flow, this pressure condition will be sensed by the sensing venturi assembly 216 which is connected to the sequencing servo cartridge 238. As also pointed out previously, this pressure is being measured by the manometer 143. When a sufficient pressure is in the chamber opposite the diaphragm in the sequencing servo cartridge, the master shaft 239 will be moved upwardly as viewed in FIG. 11 to move the valve member 247 into a closed position with respect to the valve seat to terminate the flow of source gases through the sequencing servo cartridge and thus substantially terminating the inspiratory flow.

However, in the present invention and as described in copending application Ser. No. 499,554, filed Aug. 22, 1974, now U.S. Pat. No. 3,915,164 there is provided a "topping low flow" which is introduced into the patient's breathing circuit during the period of apneustic hold which is encountered after termination of the inspiratory phase.

When the inspiratory pressure is applied to the diaphragm 326 of the apneustic plateau cartridge 317 through the tube 329, the valve member 322 is moved to the left as viewed in FIG. 11 against the force of spring 323 to permit source gas under pressure to enter the manifold 346.

The source gas in the manifold 346 normally keeps the check valve 353 in a closed position. However, in the event of failure of the apneustic plateau cartridge to operate, source gas under pressure is supplied from the inspiratory flow rate control valve assembly 358 through the tube 354 and through the one-way check valve 353 through the tube 352 and to the manifold 356. Thus, it can be seen that the one-way check valve 353 only permits flow through the same when the pressure of the inspiratory gases from the flow rate control valve 358 is greater than the source gas pressure in the manifold 346. In addition, it can be seen that the additional flow path provided through the check valve 353 provides a fail-safe feature in the event the apneustic plateau cartridge fails to operate.

A similar fail-safe circuit is provided on the other side of the flow rate control valve assembly 358 which also becomes operative if there is insufficient apneustic flow whereby flow of gas occurs through the tube 374, the check valve 373, tube 372, fitting 371 and thence through the tube 376 to the inspiratory service socket 378. Again, the check valve 373 only operates when the pressure of the gas from the manifold 346 through the restricted orifice 368, the tube 369 and the tee 371 and the tube 376 to the socket 378, is less than the inspiratory gas pressure delivered to the other side of the check valve 373 by the tube 374.

The apneustic flow gases in the manifold 346 are supplied through the tube 393, through the check valve assembly 394, the tube 396 and thence through the expiratory time control valve assembly 399 through the tube 406, the reservoir 407, tube 411 to the chamber 439 to load the diaphragm 436 to hold the expiratory termination cartridge in a closed position. Similarly, the apneustic flow gases are supplied through the tube 381, the check valve 382, the tube 383 to the expiratory flow gradient delay valve assembly 387 and through the tube 444 to the chamber 439 to load the diaphragm 436 to hold the expiratory flow gradient delay cartridge 447 is a closed position. Apneustic flow gases are also supplied through the tube 366, through the orifice 368, through the tube 369 and through the tee 371 and the tube 376 to the inspiratory service socket 378.

At the sequencing of the servo controller or the servo cartridge 238 after the end of the inspiratory phase, source gas will no longer be supplied through the apneustic flow time control valve assembly 333 to the chamber 327 of the apneustic plateau cartridge. However, at the time of this sequencing, a certain volume of gas will still be present in the chamber 327 which is at the pressure of the inlet source gas. Before the valve member 322 can be moved to a closed position under the force of the spring 323, it is necessary that the pressure of the gas in the chamber 327 be bled down through the secondary jets 189 through the apneustic flow time control valve assembly 333 through the tube 343, the tee 311, and through the venturi passage 189 and through the master venturi assembly 181. The time required to bleed down the chamber 327 sufficiently so as to permit the spring 323 to move the valve 322 to a closed position is determined by adjustment of the knob 334 of the apneustic flow time control valve assembly 333. Thus, until the apneustic platesu cartridge 317 moves to a closed position, source gas under pressure will be supplied through the master on-off switch 69 and through the tube 101, tube 236, tube 256, tube 314, past the control valve 322 of the apneustic plateau cartridge 317 and into the manifold 346. The gas then flows through the tube 366, the restricted orifice 367, tube 369, tee 371, tube 376, to the inspiratory service socket 378. This flow through the socket 378 is restricted by the orifice 368 and provides only sufficient flow to keep the exhalation valve assembly 486 in a closed position after the sequencing servo cartridge 238 has switched to the exhalation phase. The bleed-down through the venturi adds to the apneustic flow. The main topping flow is added through the inspiratory power socket 378. This pressure not only keeps the exhalation valve closed but through the nebulizer jet keeps adding gas into the patient circuit.

The flow accelerator cartridge 258 moves to a closed position immediately after sequencing of the sequencing servo cartridge 238 to terminate the inspiratory phase. This occurs because the chamber 298 is dumped immediately to the atmosphere through the check valve 286 through the tube 313 to the master venturi assembly 180 and thence through the exhalation valve assembly 486. Thus, all flow through the flow acceleration cartridge 258 and through the flow rate valve 358 is terminated immediately upon termination of the inspiratory phase.

With the present ventilator, a post-inspiratory apneustic plateau ranging from 0.25 to 3 seconds in duration can be provided by adjustment of the control knob 334 of the apneustic flow time control valve assembly 333. In this way it is possible to further enhance the total inspiratory distribution of respiratory gases transporting topically active aerosols. By way of example, it has been found that during apneustic flow approximately 200 cc of inspiratory gas is delivered per second so that during a maximum 3 second apneustic plateau, as much as 600 cc of dense aerosol can be delivered to the patient's lungs. Thus, it can be seen that during the initial inspiratory flow the humidity deficients are resolved, whereas during apneustic flow a larger particle high volume aerosol is delivered in the tracheobronchial tree to effectively enhance the mobilization of retained trachael bronchial secretions.

From the foregoing, it can be seen that a "topping low flow" is introduced into the patient's breathing circuit during the period of apneustic hold which is encountered after termination of the inspiratory phase. Decreasing the apneustic flow time increases the rate of flow of bleed-down gases from the chamber 327 through the valve 333, through the tube 343 into the secondary jets or passages 189 of the master venturi assembly 181; and conversely increasing the apneustic flow time decreases the rate of flow of bleed-down gases through the secondary passages 189 of the master venturi assembly 181 during the apneustic plateau. Also, there is an analog tapering off of the rate of the flow of bleed-down gases near the end of the apneustic plateau which creates a gradual pressure drop within the physiological system of the patient to prevent an abrupt rapid expiratory flow. These latter features are important because they make it easy to teach the patient how to use the ventilator to provide a satisfactory apneustic plateau.

When the gas has bled down sufficiently from the apneustic plateau cartridge 317 to permit the valve member 322 to move to a closed position, gas will no longer be supplied to the inspiratory service socket 378 and, therefore, the exhalation valve assembly 486 will be permitted to open thereby permitting the patient to exhale through the exhalation valve assembly 486. The exhalation gases from the exhalation valve assembly 486 are exhaled through the vapor trap assembly 487. As pointed out in copending application Ser. No. 499,544, filed Aug. 22, 1974, now U.S. Pat. No. 3,915,164 the vapor trap assembly can include a flapper valve which causes the patient to breathe or exhale against a graded positive pressure, as for example, 3 cm of water. As pointed out therein, the flapper valve is of a type which serves to retard the flow of gases very little at peak flows of gases but does serve to retard the flow of gases at slow rates of flow. In this way, the vapor trap assembly 487 does provide a retard function in addition to collecting vapors from the exhalation gases. The vapor trap assembly can be disassembled and emptied when necessary.

As soon as the patient has completed exhalation and attempts to inhale, a sub-ambient condition will be created within the breathing tube receptacle 227 which will be sensed by the sensing venturi assembly 216 to commence the inspiratory phase in the manner hereinbefore described.

However, in the event it is difficult for the patient to start the inspiratory cycle, means is provided in the ventilator for causing this to occur automatically. At the time that the apneustic plateau cartridge 317 moves to the closed or off position, source gases are no longer supplied through the tubes 381 and 393 to the chamber 439 on the back sides of the diaphragms 436 of the cartridges 413 and 447. As pointed out previously, it is at this time that the exhalation valve assembly 486 is permitted to open. Thereafter the gases in the chamber 439 behind the diaphragms 436 are bled off slowly. Thus, the gas behind the diaphragm 436 in the expiratory termination cartridge 413 and in the reservoir or accumulator 407 is bled through the tube 406, through the adjustable restricted orifice provided in the expiratory time control valve assembly 399 and then through the tube 403, the fitting 389, the tube 391, which can be considered to be a scavenging line 391 to the breathing tube receptacle 227 and out through the mouthpiece assembly and to be exhausted to the atmosphere through the exhalation valve assembly 486. Similarly, the gas behind the diaphragm 436 in the expiratory flow gradient delay cartridge 447 is bled off through the adjustable orifice provided in the expiratory flow gradient delay control valve assembly 387 through the fitting 389, through the same scavenging line 391 to the atmosphere as hereinbefore described.

As soon as sufficient gas has been bled off from behind the diaphragm 436 of the expiratory termination cartridge, the spring 431 moves the valve 434 to an open position to permit source gas to flow from the line 421 through the line 429 to supply source gas through the nozzle 222 of the serving or sensing venturi assembly 216. The gas jetting from the nozzle 222 creates a sub-ambient condition in the throat of the venturi assembly 216 which sub-anbient condition is conveyed through the tube 252 to the sequencing servo cartridge 238 to cause it to switch to the on position to commence the inspiratory phase in the manner hereinbefore described.

During the exhalation phase and prior to the commencement of the inspiratory phase, the gases will have been bled off from behind the diaphragm 436 of the expiratory flow gradient delay cartridge 447 at a rate determined by adjustment of the control valve 387. The valve 424 will then be moved to the open position under the force of the spring 431 to permit source gas to be supplied from the tube 452 through the cartridge 447 through the tube 454 to the expiratory flow gradient control valve assembly 456 through the tube 459 to the expiratory gradient service socket 462. This causes gas to be supplied through the tube 496 to the supply gases to the tee 483 to create a venturi effect within the tee 483 which establishes a negative pressure in the exhalation valve assembly that serves to aspirate exhalation gases from the mouthpiece 484 and from the lungs of the patient during the terminal portion of the expiratory phase.

Alternatively, when the tube 496 is connected to a pneumatic belt of the type described in U.S. Pat. No. 3,454,000, the gases inflate the belt to cause pressure to be applied to the chest cavity of the patient to assist the patient in emptying his lungs during the terminal portions of the expiratory or exhalation phase of the ventilator.

It is apparent from the foregoing that there has been provided a new and improved ventilator which has many improved and important features. It includes flow acceleration means which can be utilized for augmenting the flow of gases during the inspiratory phase. Flow acceleration is initiated relatively rapidly and when required but is not substantially instantaneous. The flow acceleration is adjustable so that flow acceleration will not occur below a predetermined pressure in the inspiratory circuit so that for low flow rates in the inspiratory circuit flow acceleration does not occur.

A sensing servo venturi is provided to sequence the servo cartridge into the inspiratory phase even though there may be high constant positive pressure existing within the inspiratory circuit or patient circle ranging from ambient to 60 cm of $H_2O$. Means is also provided for an apneustic or topping flow at the end of the inspitatory phase and includes means which is fail-safe in the event the apneustic plateu cartridge should fail to operate. An entrainment reservoir is provided to ensure that a sufficient supply of properly mixed gases is available to the patient during the inspiratory phase. A demand flow accelerator valve is utilized for keeping the entrainment reservoir filled so an adequate supply is available at the commencement of each inspiratory phase. An expiratory flow gradient delay circuit is provided for assisting exhalation during the terminal portion of the expiratory phase.

In addition, it can be seen that the ventilator is of a type which is relatively simple in construction. It is of the modular type and can be readily assembled. Also, it can be readily disassembled for cleaning and repair.

I claim:

1. In a method for ventilating a patient through the use of a patient adapter from a source of gas under pressure, supplying a main flow of inspiratory gas through an inspiratory flow rate control valve assembly to the patient adapter during the inspiratory phase, adjusting the inspiratory flow rate control valve assembly to adjust the main flow of gas, supplying after a predetermined period of time dependent on the insufficiency of the main flow of gas to meet the requirements of the patient, additional inspiratory gas through a flow accelerator cartridge movable between open and closed positions to the patient adapter, supplying gas from the main flow of gas to the flow accelerator cartridge to cause the flow accelerator cartridge to move from a closed position to an open position after said predetermined period of time, adjusting the flow accelerator cartridge so that it only augments the main flow of gas after elapse of said predetermined period of time whereby prior to the elapse of said predetermined period of time the inspiratory flow rate will be determined exclusively by the inspiratory flow rate control valve assembly, entraining source gas during the expiratory phase in an entrainment reservoir for a predetermined time as determined by demand until the entrained gas reaches a predetermined pressure and utilizing the entrained gas during the inspiratory phase to form a portion of the main flow of gas to the patient adapter.

* * * * *